(12) United States Patent
Krumsiek et al.

(10) Patent No.: US 9,572,633 B2
(45) Date of Patent: Feb. 21, 2017

(54) INSTRUMENT HOLDER

(71) Applicant: Gebr. Brasseler GmbH & Co. KG, Lemgo (DE)

(72) Inventors: Michael Krumsiek, Lemgo (DE); Stefan Tuenker, Lemgo (DE); Stefan Neumeyer, Eschlkam (DE)

(73) Assignee: Gebr. Brasseler GmbH & Co. KG, Lemgo (DE)

( * ) Notice: Subject to any disclaimer, the term of this patent is extended or adjusted under 35 U.S.C. 154(b) by 496 days.

(21) Appl. No.: 14/048,621

(22) Filed: Oct. 8, 2013

(65) Prior Publication Data

US 2014/0100555 A1    Apr. 10, 2014

(30) Foreign Application Priority Data

Oct. 10, 2012 (DE) .................... 10 2012 019 852

(51) Int. Cl.
| | | |
|---|---|---|
| *A61C 1/10* | (2006.01) | |
| *A61B 17/00* | (2006.01) | |
| *A61B 17/3211* | (2006.01) | |
| *A61B 17/14* | (2006.01) | |
| *A61B 90/00* | (2016.01) | |

(52) U.S. Cl.
CPC ............ *A61C 1/10* (2013.01); *A61B 17/00* (2013.01); *A61B 17/3211* (2013.01); *A61B 17/14* (2013.01); *A61B 2017/0046* (2013.01); *A61B 2090/0801* (2016.02); *A61B 2090/0813* (2016.02)

(58) Field of Classification Search
CPC ... A61C 1/10; A61B 17/00; A61B 2017/0046; A61B 2090/0813

USPC ........... 606/1–19; 433/37–64, 82–85, 91–94, 433/114, 126–135, 141, 146–147, 433/152–155, 162, 165; 425/318
See application file for complete search history.

(56) References Cited

U.S. PATENT DOCUMENTS

| | | | |
|---|---|---|---|
| 4,811,843 A | 3/1989 | Stribiak | |
| 5,057,119 A | 10/1991 | Clark et al. | |
| 7,578,819 B2 * | 8/2009 | Bleich ............... | A61B 17/1626 600/554 |
| 2002/0151891 A1 | 10/2002 | Glenn et al. | |
| 2002/0166227 A1 * | 11/2002 | Holland ................. | B25B 27/10 29/759 |
| 2005/0240120 A1 | 10/2005 | Modesitt | |
| 2006/0004398 A1 | 1/2006 | Binder et al. | |

(Continued)

FOREIGN PATENT DOCUMENTS

| | | |
|---|---|---|
| DE | 4243411 | 6/1994 |
| DE | 69122883 | 5/1997 |

(Continued)

OTHER PUBLICATIONS

Beads & Things, "Bead Shapes", published Feb. 2, 2007, http://athensbeadsandthings.com/Beads/Shapes/BeadShapes.html.*

(Continued)

*Primary Examiner* — Lynsey Crandall
*Assistant Examiner* — Jonathan Kuo
(74) *Attorney, Agent, or Firm* — Shuttleworth & Ingersoll, PLC; Timothy J. Klima

(57) ABSTRACT

An instrument holder includes a substantially tubular base body which includes a grip portion and an instrument holding portion. The base body includes a through recess extending over an entire length thereof, and the instrument holding portion includes a front-sided insertion opening designed for insertion of an instrument.

6 Claims, 2 Drawing Sheets

(56) References Cited

U.S. PATENT DOCUMENTS

| | | | |
|---|---|---|---|
| 2008/0122148 A1 | 5/2008 | Frey et al. | |
| 2008/0157488 A1 | 7/2008 | Kullmer et al. | |
| 2008/0213722 A1* | 9/2008 | Hofer | A61C 1/10 433/131 |
| 2010/0160812 A1 | 6/2010 | Jordan et al. | |
| 2010/0252467 A1 | 10/2010 | Cote et al. | |
| 2013/0071507 A1* | 3/2013 | Scheller | A61F 9/00823 425/318 |

FOREIGN PATENT DOCUMENTS

| | | |
|---|---|---|
| DE | 10146905 | 7/2003 |
| EP | 1346746 | 9/2003 |
| WO | 94/27511 | 12/1994 |

OTHER PUBLICATIONS

European Search Report dated Sep. 25, 2014 from counterpart app No. 13180909.7.

* cited by examiner

INSTRUMENT HOLDER

This application claims priority to German Patent Application DE102012019852.3 filed Oct. 10, 2012, the entirety of which is incorporated by reference herein.

DESCRIPTION

The present invention relates to an instrument holder which serves to hold a dental instrument or a medical instrument and serves to enable the handling thereof.

In the dental field or the field of dental medicine, instruments have to be handled, for instance for inserting them into or for removing them from an angle piece or a similar drive device. The instruments which may e.g. be configured in the form of saws, scalpels, or cutting tools comprise sharp cutting edges, so that special caution is required during handling. Furthermore, the instruments are often given very small dimensions, so that their handling with surgical gloves is not quite easy. Another issue is that during treatment or surgery the instruments have often to be exchanged, which requires an easy and fast handling.

It is the object of the present invention to provide an instrument holder which meets the requirements and permits a safe, simple and reproducible holding of different instruments.

This object is achieved by the feature combination described herein with the present description showing further advantageous developments.

According to the invention an instrument holder is thus provided which comprises a substantially tubular base body. The base body comprises a grip portion and an instrument holding portion. Furthermore, the base body is provided with a through recess extending over the whole length thereof. Furthermore, it is intended that the instrument holding portion comprises a front-sided insertion opening configured to introduce an instrument. Hence, it is possible to insert a dental instrument or a medical instrument into the instrument holder and thereby to hold the instrument.

The instrument holder according to the invention thus serves to hold dental instruments or medical instruments for the handling thereof. Hence, it is easily possible to insert the instruments for example into a drive device or to remove them therefrom without the instruments themselves having to be directly gripped by hand. Thus the instrument holder according to the invention is instrumental in avoiding a direct manual gripping of the instruments in that these are inserted into the instrument holder and handled together with said holder. Hence, a direct manual contact with the instruments is not needed. This excludes the risk of injury for the physician or his/her assistant. Furthermore, even very small instruments can be safely handled since the instrument holder itself is given a sufficiently great dimension so as to be gripped in a safe and comfortable manner. The instrument holder according to the invention thereby represents a multifunctional grip.

The instrument holder according to the invention further serves to handle individual instruments during their whole cycle of use. Hence, the instruments can already be made available to the dentist or surgeon in a respective instrument holder. The instruments can thus be delivered in a sterile state together with the instrument holder, so that a preceding separate manual handling is not needed. It may here turn out to be particularly advantageous when the instrument holder is provided with suitable labels or markings, e.g. also designed in colors, to inform the dentist or surgeon about the instrument disposed in the respective instrument holder. This person can then use the instrument holder together with the instrument in a drive device, e.g. an angle piece. After use of the instrument said instrument is then received by the instrument holder and removed from the drive mechanism, in a particularly advantageous configuration of the invention it is also possible to clean the instrument holder together with the instrument and to supply it to the hygiene cycle. This can prevent a manual touching of the work area of the instrument.

In a particularly advantageous configuration of the invention it is intended that the instrument holding portion is provided with at least one lateral recess. A visual inspection can be made through this recess as to whether an instrument is located in the instrument holder and which instrument is received by the instrument holder.

To captively hold the instrument in the instrument holder, it is advantageous when the insertion opening is provided with at least one elastic clamping element. Said clamping element can e.g. be configured in the form of an elastic tongue which is brought into contact with the shaft of an instrument. It is thereby prevented that the instrument will be released during handling of the instrument holder and will fall out of the holder. Preferably, several elastic clamping elements of such types are provided in the area of the insertion opening.

To improve a cleaning of the instruments, it may be advantageous when at least one rinsing recess is formed in the area of the insertion opening. A cleaning fluid can be passed by way of this rinsing recess through the inner portion of the instrument holder so as to clean the instrument itself.

The grip portion is preferably provided with a recessed grip so as to be able to grip the instrument holder safely and reliably also under complicated handling conditions, for instance with surgical gloves.

An intermediate portion which is shaped as an annular bead is formed in an advantageous development of the invention between the grip portion and the instrument holding portion. Said intermediate portion also serves to apply axial forces so as to be able to insert or remove the instrument into or from a drive mechanism (e.g. an angle piece) by means of the instrument holder. Moreover, a safe handling of the instrument holder itself is thereby achieved.

The grip portion is preferably configured such that it is suited for accommodating the instrument holder in a tray and/or is insertable into a disinfecting device or an associated auxiliary device.

Furthermore, it may be advantageous when the instrument holding portion is provided with an anti-twist device, so that an exact assignment of the instrument is possible.

The instrument holder according to the invention can be made from different materials, e.g. from medically approved plastics, such as PEEK or LPC. It is however also possible to make the instrument holder from metallic materials, such as titanium, titanium alloys or special steel.

As has been described above, it is thus possible through a suitable selection of the material of the instrument holder to introduce the instrument holder together with an instrument into a thermal disinfector so as to clean or disinfect the instrument holder together with the instrument. As has been mentioned, a rinsing and cleaning fluid can be passed through the instrument holder.

At the free end portion the instrument holder according to the invention comprises preferably at least one bending slit adjacent to the insertion opening. It is thereby possible that during treatment the dentist can grip and bend the instrument with the instrument holder so that the instrument can be adapted to the anatomic shape of the tooth to be treated.

The invention will now be described with reference embodiments in combination with the drawing, in which.

Like members are provided with like reference numerals in the following embodiments.

Figure 1:
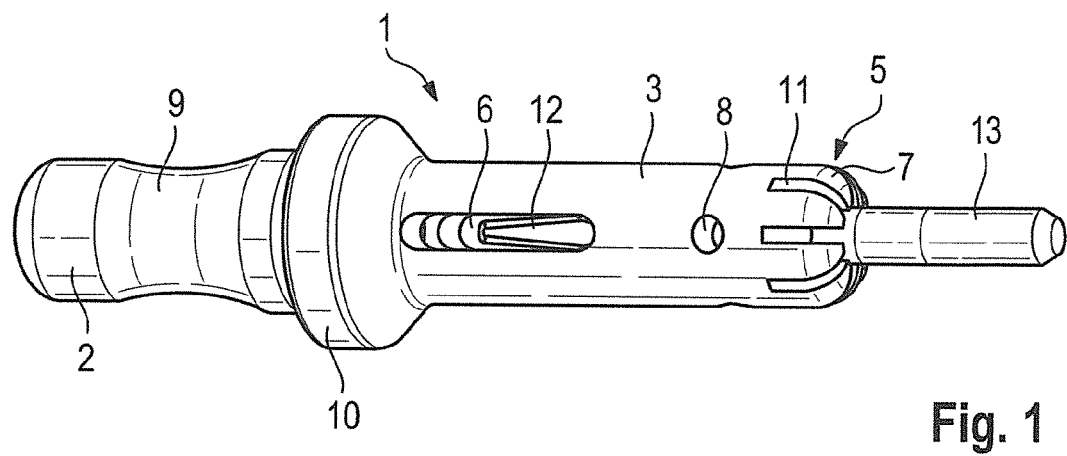
FIG. 1 is a perspective view of a first embodiment of an instrument holder according to the invention with inserted instrument.

According to a first embodiment the instrument holder according to the invention comprises a substantially tubular base body 1 which is provided with a grip portion 2 and an instrument holding portion 3. An intermediate portion 10 which is shaped as an annular bead and has an enlarged diameter is provided between the grip portion 2 and the instrument holding portion 3. The grip portion 3 is provided with a recessed grip 9.

Figure 2:
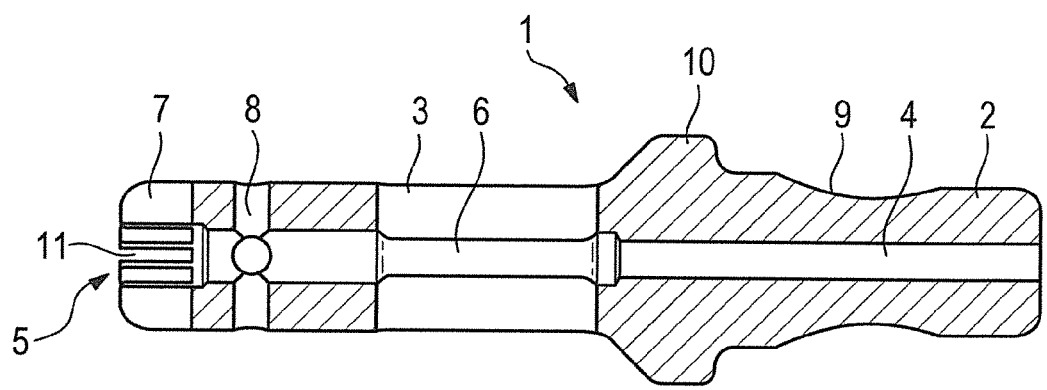
FIGS. 2 and 3 are axial sectional views of the embodiment of the instrument holder as shown in FIG. 1.
Figure 3:
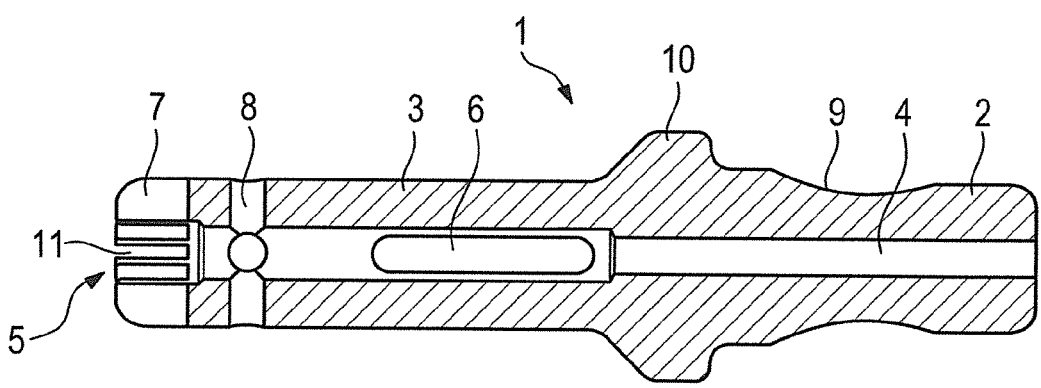

A through recess 4 extends through the whole length of the instrument holder according to the invention (see FIGS. 2 and 3).

Plural clamping elements 7 which are designed in the form of elastic fingers are formed at the free end of the instrument holding portion 3. Bending slits 11 are provided between said clamping elements 7.

The instrument holding portion 3 comprises lateral recesses 6 which serve as viewing windows.

As shown in FIG. 1, a dental instrument or medical instrument can be inserted through a front-sided insertion opening 5 into the through recess 4 of the instrument holder. A work head 12 of the instrument is here positioned in the inserted state such that it is located in the portion of the lateral recesses 6. One can thus see the work head through these recesses just like through an inspection window so as to check the position thereof on the one hand and to determine on the other hand whether the correct instrument is disposed in the instrument holder. A shaft 13 of the instrument is thereby clamped and held by the clamping elements 7 so as to prevent the instrument from inadvertently falling out.

Furthermore, in the area of the instrument holding portion the figures show additional rinsing recesses 8 through which a cleaning or rinsing fluid can be introduced or discharged.

Figure 4:
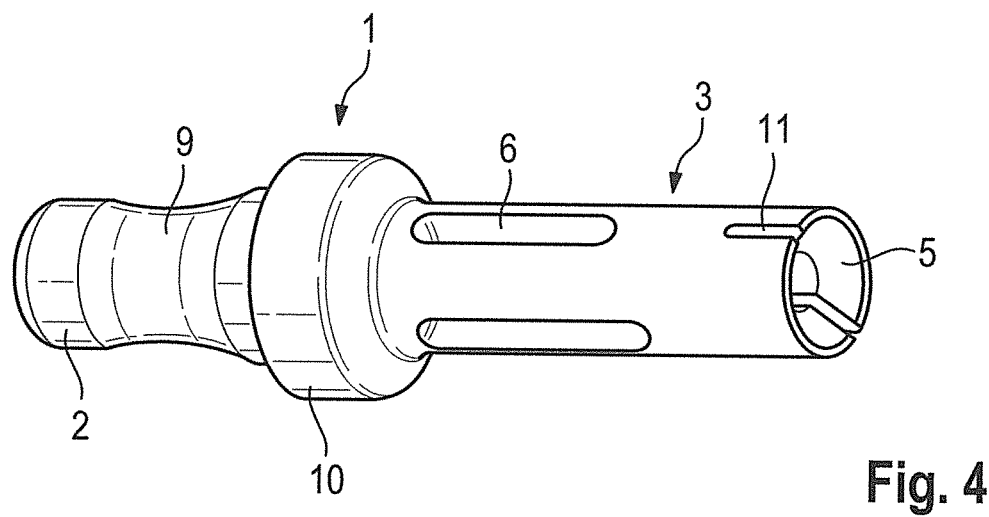
FIG. 4 is a perspective view, similar to FIG. 1, of a further embodiment.
Figure 5:
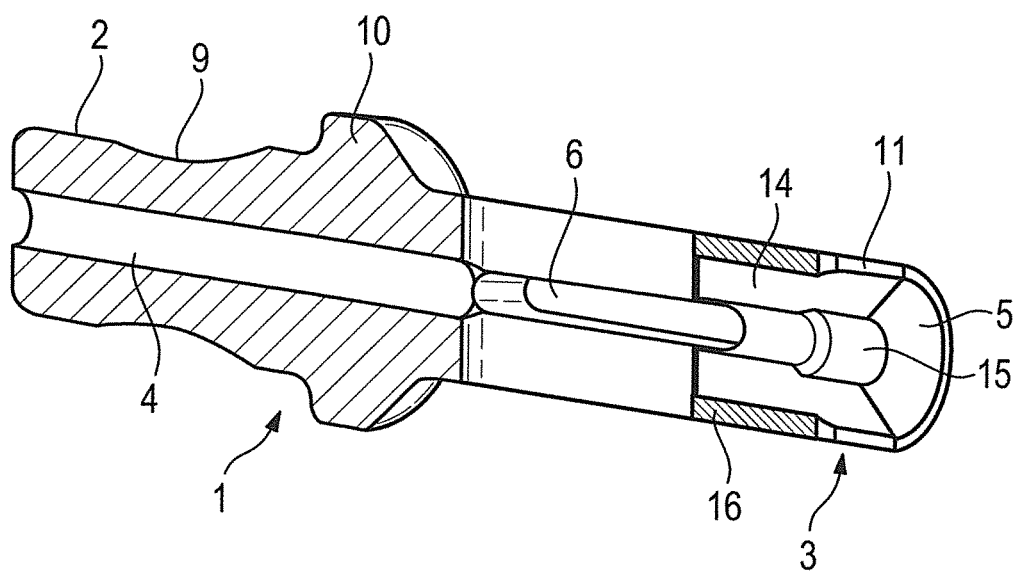
FIG. 5 is a sectional view of the embodiment shown in FIG. 4.

FIGS. 4 and 5 show a further embodiment of the invention. This embodiment differs from the embodiment of FIGS. 1 to 3 with respect to the configuration of the insertion opening. This opening is funnel-shaped to facilitate introduction of an instrument. Furthermore, two bending slits 11 that are opposite to one another are provided adjacent to the funnel-shaped insertion opening 5; like in the embodiment of FIGS. 1 to 3, these make it possible to bend an instrument.

The through recess 4 extends through the whole length of the base body 1, by analogy with the configuration according to FIGS. 1 to 3. In the instrument holding portion 3, the through recess 4 is enlarged, thereby forming an enlarged portion 14 (FIG. 5). The through recess 4 is provided with an enlarged diameter also adjacent to the funnel-shaped insertion opening 5, as is shown by reference numeral 15. The enlarged portion 14 is formed in extension of the bending slits 11, so that the instrument holding portion 3 encompasses the webs 16, as shown in FIG. 5, and is defined by the same.

LIST OF REFERENCE NUMERALS

1 Base body
2 Grip portion
3 Instrument holding portion
4 Through recess
5 Insertion opening
6 Lateral recess
7 Clamping element
8 Rinsing recess
9 Recessed grip
10 Intermediate portion
11 Bending slit
12 Work head
13 Shaft
14 Enlarged portion
15 Diameter portion
16 Web

The invention claimed is:

1. An instrument holder comprising:
a substantially tubular base body which includes a grip portion and an instrument holding portion,
the base body comprising a through recess extending over an entire length thereof, and
the instrument holding portion including a front-sided insertion opening for insertion of an instrument;
at least one rinsing recess formed in an area of the insertion opening;
wherein the instrument holding portion includes at least one lateral recess positioned between the at least one rinsing recess and an end of the grip portion opposite the front-sided insertion opening;
wherein the insertion opening includes at least one elastic clamping element positioned at the front-sided insertion opening, the at least one elastic clamping element being externally exposed and including a fixed end connected to the instrument holding portion and a free end extending in a cantilever manner outwardly in an axial direction from the instrument holding portion, the at least one elastic clamping element having an elasticity that provides a biasing force directed radially inwardly toward the insertion opening.

2. The instrument holder according to claim 1, wherein the grip portion includes at least one recessed grip.

3. The instrument holder according to claim 1, and further comprising an intermediate portion shaped as an annular bead positioned between the grip portion and the instrument holding portion.

4. The instrument holder according to claim 1, wherein the grip portion is configured to receive the instrument holder in a disinfection device.

5. The instrument holder according to claim 1, wherein the instrument holding portion includes an anti-twist device.

6. The instrument holder of claim 1, wherein the at least one elastic clamping element includes a plurality of elastic clamping elements positioned around a circumference of the front-sided insertion opening and separated by a plurality of circumferentially arranged and axially extending bending slits, each of the plurality of elastic clamping elements being externally exposed and including a fixed end connected to the instrument holding portion and a free end extending in a cantilever manner outwardly in an axial direction from the instrument holding portion, each of the plurality of elastic clamping elements having an elasticity that provides a biasing force directed radially inwardly toward the insertion opening.

\* \* \* \* \*